(12) United States Patent  
Vigen (10) Patent No.: US 11,774,382 B1  
(45) Date of Patent: Oct. 3, 2023

(54) SYSTEM AND METHOD FOR TARGETED RE-EXAMINATION, INNER LAYER DEFECT ANALYSIS, PROTEIN IDENTIFICATION, AND PHOTON COMPUTER

(71) Applicant: Eric Arno Vigen, Lucas, TX (US)

(72) Inventor: Eric Arno Vigen, Lucas, TX (US)

(*) Notice: Subject to any disclaimer, the term of this patent is extended or adjusted under 35 U.S.C. 154(b) by 374 days.

(21) Appl. No.: 17/139,271

(22) Filed: Dec. 31, 2020

Related U.S. Application Data

(60) Provisional application No. 62/955,499, filed on Dec. 31, 2019.

(51) Int. Cl.
| | | |
|---|---|---|
| *G01N 23/225* | (2018.01) | |
| *G01N 33/68* | (2006.01) | |
| *H01J 37/06* | (2006.01) | |
| *H01J 37/244* | (2006.01) | |
| *G01N 23/2251* | (2018.01) | |

(52) U.S. Cl.
CPC ..... *G01N 23/2251* (2013.01); *G01N 33/6803* (2013.01); *H01J 37/06* (2013.01); *H01J 37/244* (2013.01); *H01J 2237/2445* (2013.01)

(58) Field of Classification Search
CPC . G01N 23/2251; G01N 33/6803; H01J 37/06; H01J 37/244; H01J 2237/2445
See application file for complete search history.

(56) References Cited

U.S. PATENT DOCUMENTS

2012/0002783 A1* 1/2012 Toyokawa ........... G01V 5/0008  
378/57

* cited by examiner

*Primary Examiner* — Mark R Gaworecki  
(74) *Attorney, Agent, or Firm* — Mark L. Cooper (57) ABSTRACT

A system includes a target object for examination; electrical transfer points associated with the target object, the electrical transfer points being an application of energy to generate one or more photons; devices for receiving and measuring electromagnetic waves from the one or more photons, to generate a data set of information, the information including at least one of direction, wavelength, and polarity; a computer having a platform to receive the data set of information; generate a model of subatomic particle placement for the photons, as determined by the data set of information; and re-examine the model at one or more of a different initiation-to-destination energy path, a different measuring position, or a different energy input; the receiving of the data set of information, generating of the model, and the re-examination of the model provides information for industrial application.

12 Claims, 5 Drawing Sheets

FIG. 1

(Prior Art)

| Optical Type | Wavelength | Frequency | Energy | Microscopy Technique | Applicable Subatomic Interaction |
|---|---|---|---|---|---|
| Sonogram | Calc by Medium | 2.0E+04 / second | | Sonogram | Living organs |
| Radio Waves | Calc by Medium | E+06 to E+08 / second | | Radio | |
| Microwaves | Calc by Medium | E+10 / second | | Microwaves | |
| Infra-Red (IR) | 1pm (E-06 m) | 3.E+14 / second | 0.1eV | | Molecular Bond Distance– Spectrum-1 |
| Visible Light (VL) | 400-700 nm (~6.E-07 m) | 5.E+14 / second | 1eV | Electrostatic electron beam | Electron Binding Structure, Entanglement Nodes – Spectrum-2 |
| Ultra-Violet Light (UV) | 100 nm (E-07 m) | 3.E+15 / second | 10kv | Gas ionization | |
| Ultra-Violet Light (UUV) | 10 nm (E-08 m) | 3.E+16 / second | 10kv | Tomography | Band gap - Insulator |
| X-Rays | 1nm (E-09 m) to 1nm (E-11 m) | 3.E+17 to E+19 / second | 1000kv | SEM | Subatomic Particle Diameter |
| Gamma Rays | 1nm (E-12 m) | 3.E+20 / sec | 1000Mv | None exist | Subatomic Particle Orientation or Rotation |

SYSTEM AND METHOD FOR TARGETED RE-EXAMINATION, INNER LAYER DEFECT ANALYSIS, PROTEIN IDENTIFICATION, AND PHOTON COMPUTER

BACKGROUND

1. Field of the Invention

The present invention relates generally to imaging and microscopy systems, and more specifically, to a system for examination and re-examination of materials for identification of sequenced materials. For example, the present invention provides for using energy waves to generate photons, in small, matched quantities, and with electromagnetic methods, wherein the generated photons are analyzed for information, examination, and reexamination.

2. Description of Related Art

There are a plurality of prior art microscopy techniques that each have their own associated faults.

Figure 1:
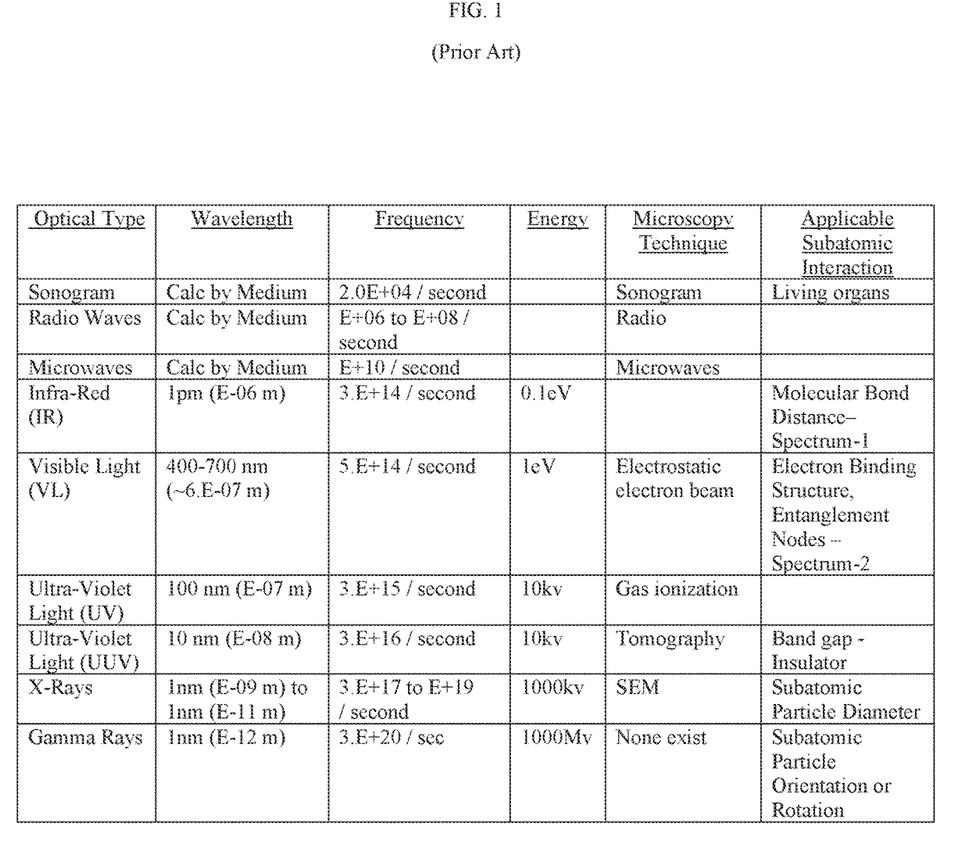
FIG. 1 is a table of optical types, wavelengths, frequency, and energy.

FIG. 1 is a table of Optical Types, their wavelength, frequency, and energy with the related microscopy technique and precision level of particle interaction discerned by that microscopy technique. These are ordered from least energy to most energy which is also lowest frequency to highest. There is an inverse relationship between those two attributes (frequency and energy) and the opposition factor of distance precision. The critical factor here is that to get more precision, one uses more energy. The present invention is methods and systems to manipulate events with lower entry to still get better precision via modelling position and orientation.

It is well established and understood that higher frequency, for smaller wavelengths, for greater precision, requires much greater energy, and has other risks, like X-Rays destroy the tissues of living beings. As such, the present invention is a method to use that dataset from a better, safer frequency level and strength, and thereby energy, lower in the scale, yet achieve precision at a higher level. That is useful to get smaller distance measurement without the excessive energy and its risks of extremely small wavelengths which require extremely high energy.

In the present invention, light, specifically each photon, becomes an information set which generate models of molecules that include 3D engineering positions for its constituent subatomic particles (protons, electrons, and neutrons), within a few electron-diameter tolerance a low temperatures, of each electrons and nucleus set of such molecule, that react with mechanical adjustments, and thereby change the particles, energy levels. This engineering in present invention teaching allow methods and uses that take the subatomic particles a) energy levels, b) positions, c) polarity and spin, which determine d) bonding strength into models which then generate further actions, which has use in i) manufacturing, and ii) information systems.

Light is powerful information. It tells the data for interactions too small for us to observe. The bright green of spring tells that lots of new chlorophyll has activated in plants without the precision of our unaided vision to discern that cell and the molecules. The unaided eye cannot observe a PS-I site in the thylakoid wall. However, the interaction of molecular bonds specific to the knowable interaction of the particles in combinations of Elements of the Periodic Table creates each set of specific color frequencies and wavelengths. The abundance of specific colors tells the macro-world about the micro-world. All this is true without microscopes, yet prior art and the present invention imaging and microscopy methods and systems generate more understanding beyond just the overall information of human vision, which operates by the general abundance (lots of green photons) of certain wavelength photons, based upon visible light, or more technically various types electromagnetic waves. There are prior art and present invention techniques to discern, gather and use more and better information, particularly tiny, subatomic dimension information of inner layer molecules as determined by the light of larger dimensions (that is lower-energy, longer-wavelength), and from that thereby to generate more precise methods for further actions.

Accordingly, although great strides have been made in the area of microscopy and imaging systems, many shortcomings remain.

It is an object of the present invention to provide for a system that utilizes lower energy, and thereby lower risk and lower cost, examination methods at the molecular and subatomic particle level. The system of the present invention gathers and validates information about molecules first as a) Position, then as b) Orientation, and finally as c) polarity relative to internal axis of the nucleus ("nucleostatic").

The preferred embodiment of the present invention combines: Causation of photons by low-energy electrostatic methods via knowable paths along, or even through. the target material. The prior art, such as STM, is excellent only as surface dimension, and nothing about internal structure. Capture and measurement of photons based upon direction, wavelength and/or polarity. Using teaching of the present invention to map such larger wavelength data-set to determine the much smaller internal molecular distance of an electron-nucleus-electron set consistent and stable for understanding the molecular structure within a range square root the distance of the wavelength data. That translation solves the precision-energy dilemma of prior art. The present invention gets precision while using lower energy than prior art. Model the target object, molecules, based upon assembly in 3D of these electron-nucleus-electron sets.

Manipulation for either or both causation and capture/measurement based upon the model and its predictions. That is a mechanical process integrated with a computerized determine management of current directions, receptors, and potentially the object not possible without the process of examine-model-re-examine of the present invention.

DESCRIPTION OF THE DRAWINGS

The novel features believed characteristic of the embodiments of the present application are set forth in the appended claims. However, the embodiments themselves, as well as a preferred mode of use, and further objectives and advantages thereof, will best be understood by reference to the following detailed description when read in conjunction with the accompanying drawings, wherein:

While the system and method of use of the present application is susceptible to various modifications and alternative forms, specific embodiments thereof have been shown by way of example in the drawings and are herein described in detail. It should be understood, however, that the description herein of specific embodiments is not intended to limit the invention to the particular embodiment disclosed, but on the contrary, the intention is to cover all modifications, equivalents, and alternatives falling within the spirit and scope of the present application as defined by the appended claims.

DETAILED DESCRIPTION OF THE PREFERRED EMBODIMENT

Illustrative embodiments of the system and method of use of the present application are provided below. It will of course be appreciated that in the development of any actual embodiment, numerous implementation-specific decisions will be made to achieve the developer's specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure.

The system and method of use in accordance with the present application overcomes one or more of the above-discussed problems commonly associated with conventional microscopy and imaging systems. Specifically, the present invention utilizes lower energy, and thereby lower risk and lower cost. These and other unique features of the system and method of use are discussed below and illustrated in the accompanying drawings.

The system and method of use will be understood, both as to its structure and operation, from the accompanying drawings, taken in conjunction with the accompanying description. Several embodiments of the system are presented herein. It should be understood that various components, parts, and features of the different embodiments may be combined together and/or interchanged with one another, all of which are within the scope of the present application, even though not all variations and particular embodiments are shown in the drawings. It should also be understood that the mixing and matching of features, elements, and/or functions between various embodiments is expressly contemplated herein so that one of ordinary skill in the art would appreciate from this disclosure that the features, elements, and/or functions of one embodiment may be incorporated into another embodiment as appropriate, unless described otherwise.

The preferred embodiment herein described is not intended to be exhaustive or to limit the invention to the precise form disclosed. It is chosen and described to explain the principles of the invention and its application and practical use to enable others skilled in the art to follow its teachings.

Figure 2:
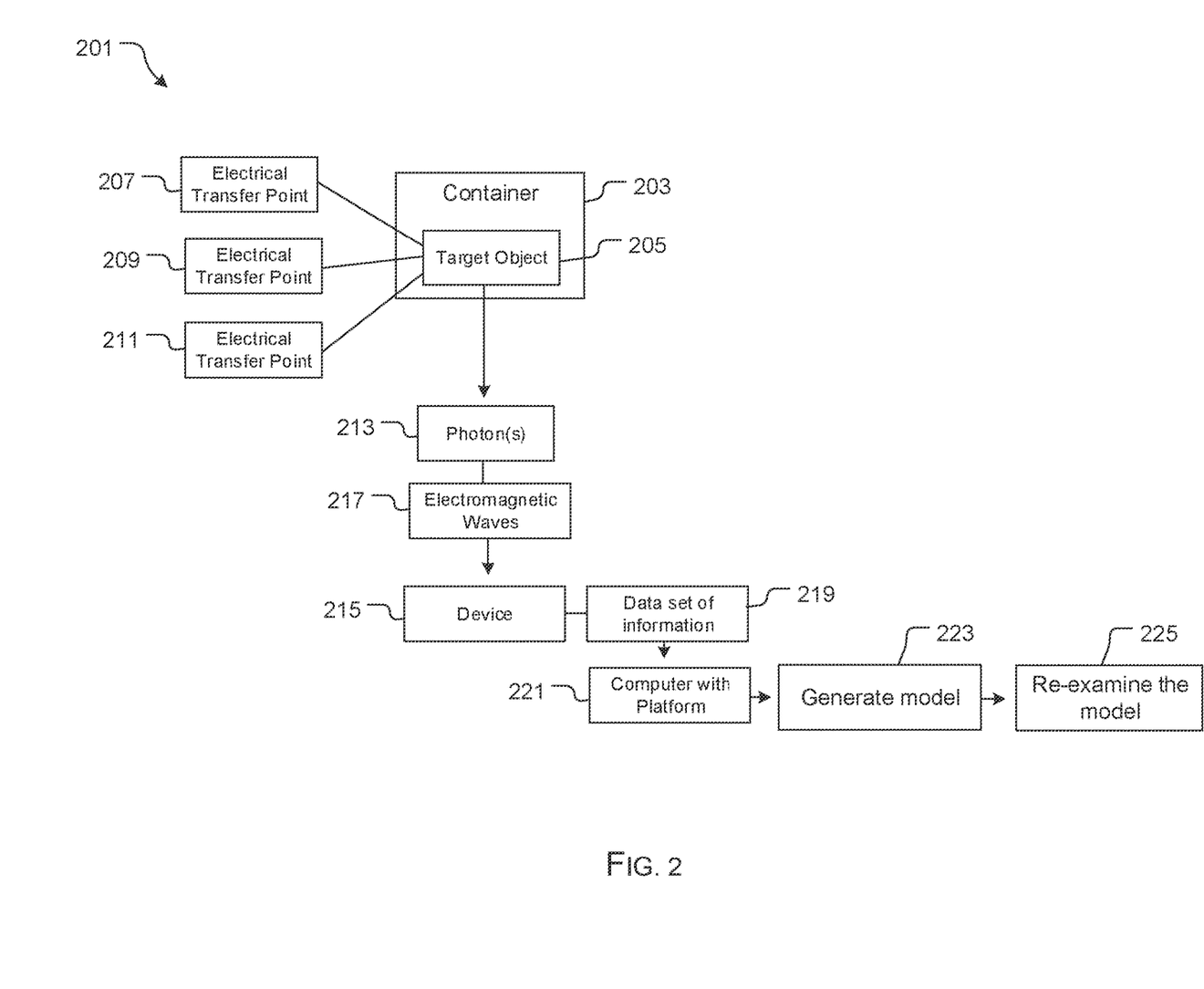
FIG. 2 is a simplified schematic of a first embodiment of a system in accordance with a preferred embodiment of the present application.
Figure 3:
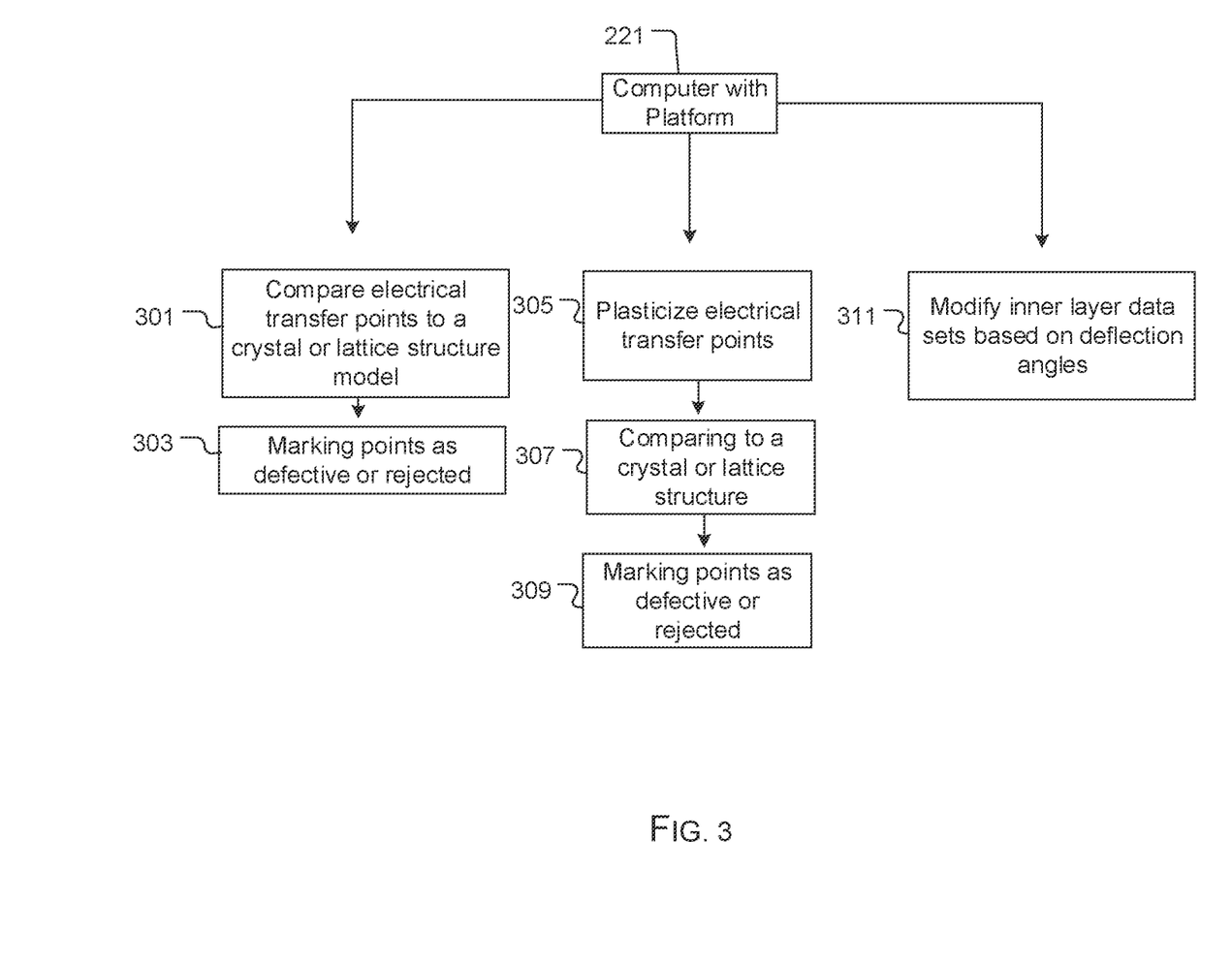
FIG. 3 is a simplified schematic of additional steps of the platform of FIG. 2.
Figure 4:
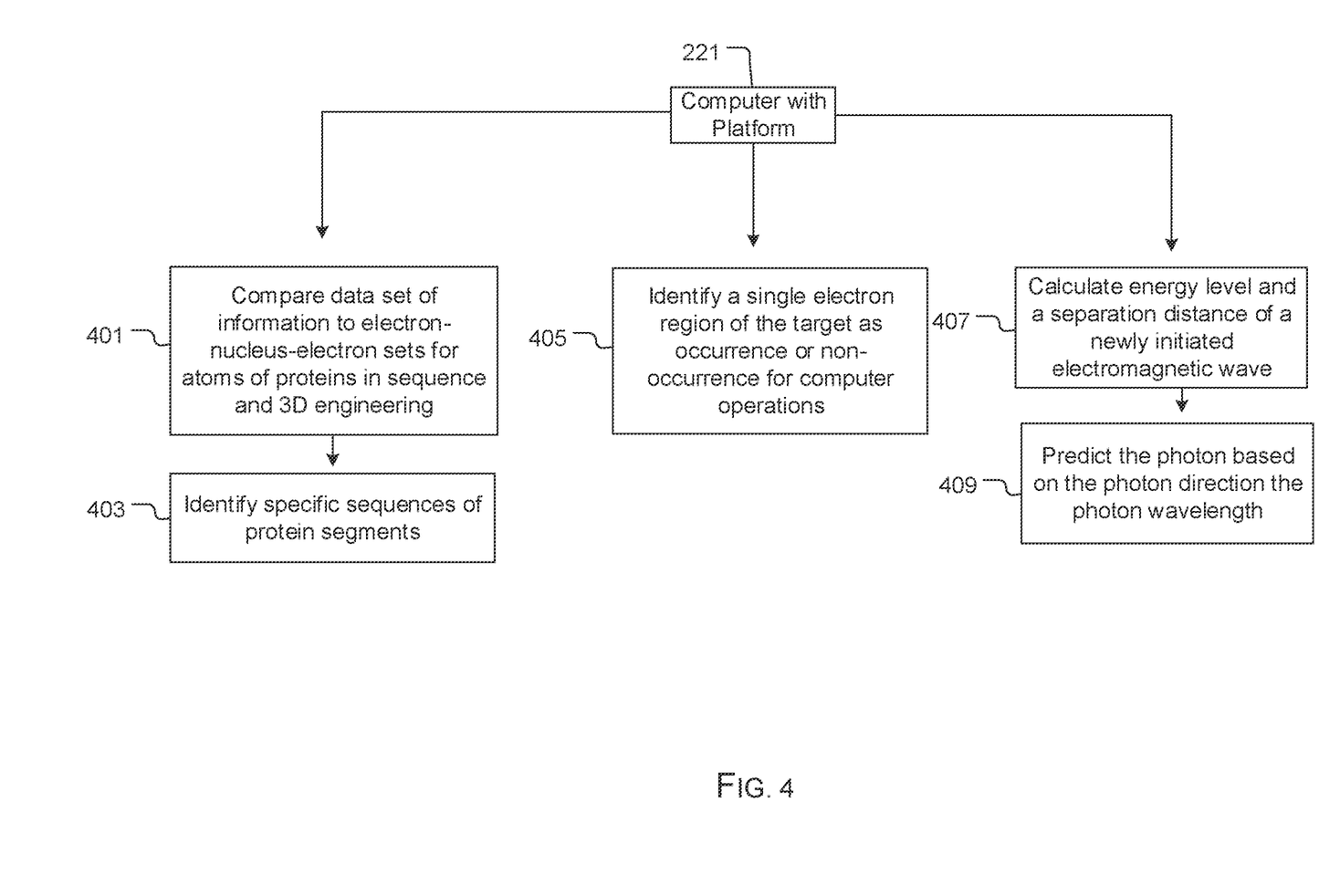
FIG. 4 is a simplified schematic of additional steps of the platform of FIG. 2.
Figure 5:
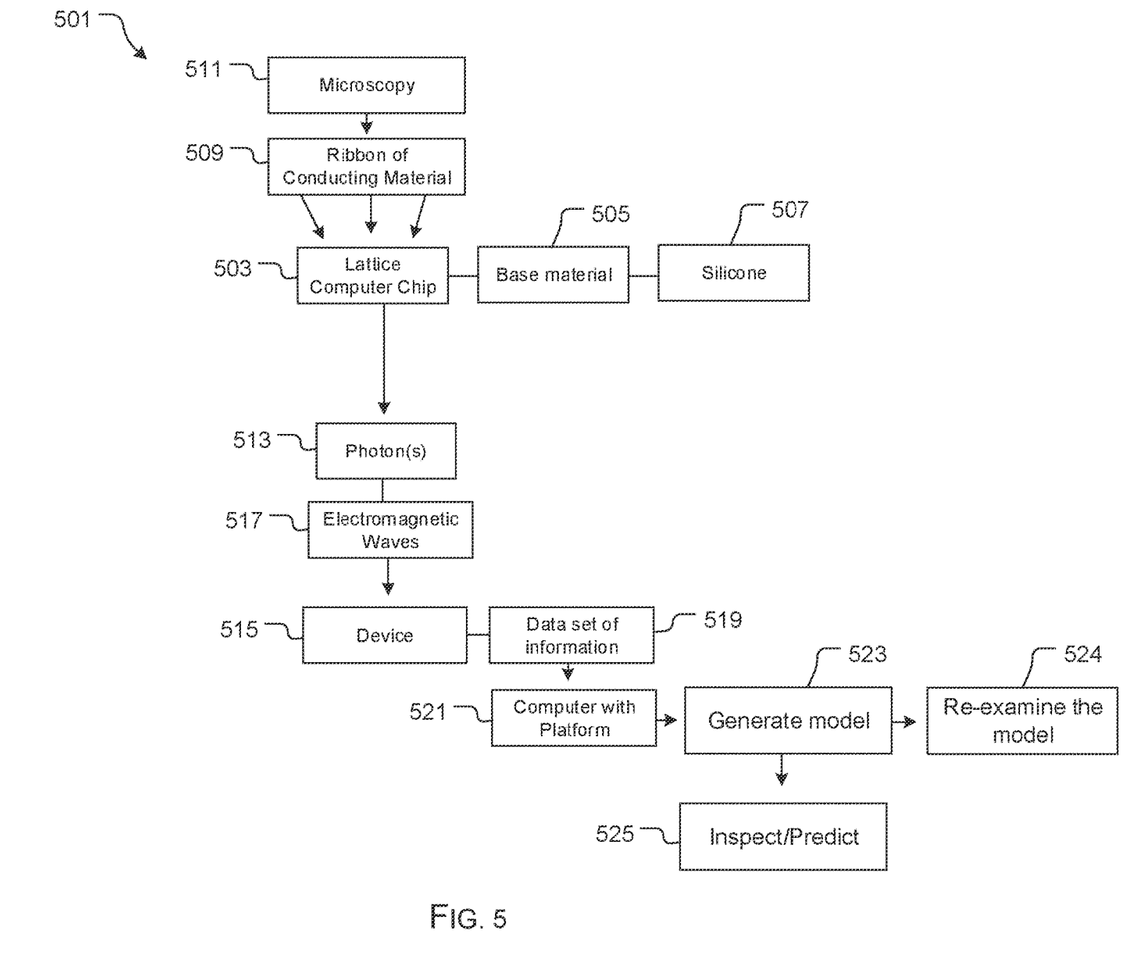
FIG. 5 is a simplified schematic of a second embodiment of a system in accordance with the present application.

Referring now to the drawings wherein like reference characters identify corresponding or similar elements throughout the several views, FIG. 2 depicts a simplified schematic of the core features and functionality of the present invention. FIGS. 3 and 4 depict additional process of the platform of FIG. 2, again within the core functionality of the present invention. FIGS. 5 and 6 depict the core features of an additional embodiment of the present invention, associated with computer chips. It should be appreciated that system 201 and system 501, as shown in FIGS. 2 and 5, are merely the core features, and further explanation of the science and functionality of the present invention will be provided later herein.

In the contemplated embodiment, system 201 includes a closeable container 203 with a target object 205 inside of the closeable container, the target object is for examination and may be any number of various objects.

The system 201 further includes a plurality of electrical transfer points 207, 209, 211 associated with the target object, the plurality of electrical transfer points being an application of energy to generate one or more photons 213, as shown.

The system 201 will further include one or more devices 215 for receiving and measuring electromagnetic waves 217 from the one or more photons, to generate a data set of information 219, the information including at least one of direction, wavelength, and polarity.

The data set of information including direction, wavelength, and polarity can further be defined as: the photon direction is a line defining the geometric engineering of the one or more sets of electron-nucleus electrons; the photon wavelength determines the 3D internal dimension of one of the one or more sets of electron-nucleus electrons; and the photon polarity is a 3D rotational direction relative to the one or more sets of electron-nucleus electrons, including subshell-s.

In the present invention, a computer 221 having a platform thereon will be used to receive the data set of information for analysis. The computer, along with the platform and associated software, will be configured to generate a model 223 and re-examine the model 225, as will be discussed in more detail herein.

The generation of the model will generate a model of subatomic particle placement for the one or more photons by one or more sets of electron-nucleus-electrons at 180 degrees versus nucleus vertex by at last one of direction, wavelength, and polarity, as determined by the data set of information. Re-examination will involve re-examining the model at one or more of a different initiation-to-destination energy path, a different measuring position, or a different energy input. The receiving of the data set of information, generating of the model, and the re-examination of the model provides information for industrial application.

It should be appreciated and understood that based on the needs of the user, the system can be adapted for further analysis and information generation. This is shown in FIGS. 3 and 4.

As shown in FIG. 3, the computer with the platform 221 can further be used for various steps. As examples, the system may be configured to compare each of the plurality of electrical transfer points to a crystal or lattice structure model, the comparing being based on knowable inclination angles of subatomic particle electron-nucleus-electron sets of the crystal or lattice structure, 301, and marking, based on the comparing, any of the plurality of electrical transfer points as defective or rejected, 303.

As further shown, the computer with the platform 221 can be configured to plasticize, by utilizing a series of examination pulses and examining variability of photon direction of the series of examination pulses, each of the plurality of electrical transfer points, 305, and compare the plasticizing to a crystal or lattice structure model, the comparing being based on knowable inclination angles of subatomic particle electron-nucleus-electron sets of the crystal or lattice structure, 307, and marking, based on the comparing, any of the plurality of electrical transfer points as defective or rejected, 309.

As further shown, the computer with the platform 221 can be configured to modify one or more inner layer data-sets of one or more inner layer target points of the plurality of electrical transfer points based upon deflection angles statistically different from one or more outer layer data sets of one or more outer layer target points of the plurality of electrical transfer points, 311.

In FIG. 4, additional examples of additional processing steps are shown. As shown, the computer and platform 221 can be configured to compare the data-set of information, including direction as it relates to inclination angles of bonds, to electron-nucleus-electron sets for atoms of proteins in sequence and 3D engineering, 401, and identify, based on the comparing, a specific sequence of protein segments associated with one or more inner layer target points of the plurality of electrical transfer points, 403.

As further shown, the computer with platform 221 can be configured to identify a single electron region of the target object as occurrence or non-occurrence for computer operations based on the model, the identification being based on electron energy level changes as a read-only memory method, 405.

As further shown, the computer with platform 221 can be configured to calculate an energy level and a separation distance of a newly initiated electromagnetic wave associated with a photon, 407, and predict the photon based on the photon direction and the photon wavelength based on the data set of information and the model, 409.

It should be appreciated that the system of the present invention can have various modifications, for example, the application of energy can occur by multiplicity of connectors, which during re-examination are switched to provide paths to a 1-atom tip via one of the plurality of electrical transfer points that pass through to inner layers of the target. Further, the application of energy occurs by multiplicity of connectors, which during re-examination are switched to provide at least two paths to a t atom tip via the plurality of electrical transfer points that are associated with a molecule, but via different positions of both the 1 atom tip and the plurality of electrical transfer points.

In FIG. 5, another simplified schematic depicts an alternative embodiment of a system 501 in accordance with the present invention. It should be appreciated that system 501 is similar in form and function to system 201, however, system 501 is the application to a computer chip specifically.

As shown, system 501 includes a lattice computer chip 503 generated from lattice, including a base material 505, which in some embodiments is silicone 507, with differential memory behavior by doping with a atoms or molecule other than such base material. The system 501 further including a ribbon of conducting material 509 placed such that electricity flows (as indicated by the plurality of arrows) to the lattice computer chip and at a range of two to four silicon molecules away. A microscopy 511 for creating electrical energy flow at a plurality of positions of different 3D orientation towards the lattice computer chip, such that one or more photons 513 are generated.

As shown, one or more devices 515 for receiving and measuring electromagnetic waves 517 from the one or more photons, to generate a data set of information 519, the information including at least one of direction, wavelength, and polarity.

The data set of information is received by a computer with a platform 521, wherein the platform 521 is configured to generate a model 523 and reexamine the model 524.

In this embodiment, the generation and re-examination includes the platform generating a model of subatomic particle placement for the one or more photons by one or more sets of electron-nucleus-electrons at 180 degrees versus nucleus vertex by ate last one of direction, wavelength, and polarity, as determined by the data set of information, and re-examination the model at one or more of a different initiation position, a different measuring position, or a different energy input. The receiving of the data set of information, generating of the model, and the re-examination of the model provides information for the lattice computer chip. A direct electrical connection to the lattice computer chip occurs by multiplicity of connectors which are switched to provide at least two paths to a 1-atom tip via the lattice computer chip that occur through the same molecule, but via different positions of both the 1-atom tip and the direct electrical connection. An intermediate electrical pulse occurs between two direct connectors in an orientation different to a direction of the 1-atom tip to direct electrical connection.

In system 501, the computer and platform 521 can provide for further inspection and predictions 525. Specifically, the computer and platform can inspect, provided an inclination angle and the data set of information, for a photon in a different direction at an angle greater than 20 degrees; and predict one or more additional target areas for examination of the lattice computer chip for different electron-nucleus-electron sets in 3D space, wherein the data set of information includes a relative angle of a predicted electron-nucleus electron 3D orientation.

The system of the present invention provides for: Enhancements to microscopy methods to avoid the harmonics that interfere with effective measurement; Use of target-generated photons as electron-nucleus-electron datasets for 3D modelling as the subatomic particle radius, and specific positions, orientations, rotations, and polarity for each subatomic particle; Initiated in photon methods and initiate by electrical flow directions; Enhancements to STM systems to target not just surface, but also directions for additional information from the same examination; Modeling that directs further action; Examination, like read-only memory, which does not disturb electron positions being the 0 or 1 in microchips.

Lattice structures of multiple materials in connection with electrical energy paths that, for target electrons, with spacing herein designed for doping sites to become information as electron position, channeled electricity with photon detection combination for read-only inspection, data update by electron movement for different channeled electricity, and lattice and 'hole' material choices to isolate and ease the inspection and transformation.

Combination of electricity current along determined direction that both a) moves target electrons, and b) reads certain sets electron placements without disturbing the electron.

The present invention includes using light, and more generally choices in a range of electromagnetic waves, a) via measuring methods b) fed into a computerized modelling system for analysis of subatomic particles and particle systems, c) triggered by 3D engineered methods for subatomic particles and particle sets, d) leading to responsive further actions. Computer methods connect to mechanical methods. The commercial goal of microscopy, especially for downstream commercial applications, includes the identification on target material locations of a) the wrong molecule in a structure, and b) the wrong orientation which leads to further actions, like rejection or marking or re-processing, or further examination. The commercial application also uses microscopy results to trigger chemical reactions changes, use the electrons as the markers for computer information, and recognize medical, pharmaceutical procedures, therapies, and medicines.

In this filing, the specification uses the word 'microscopy' broadly defined as the range of methods of observing electromagnetic waves, and their underlying fields of force, that propagate at the speed of light with wave generators and wave receptors/measurement devices to deliver information sets at the molecular level and smaller. I note that the wording 'imaging' is also commonly used, although usually not for uses with subatomic particle precision, but instead for multi-molecule structures, like organs from a mammogram. These uses of either wording overlap, and many people interchange those words, as they both are taking energy waves to create images. The choice of microscopy herein includes what many say as imaging. Finally, computer memory is a method of examining lattice structure particles which is generally more specific and discussed separately from microscopy, but computers are including the target uses of the present invention.

The system of the present invention provides for examination including: Changing the position of the photon receptor/measurement screen; Changing the polarization orientation of the photon receptor/measurement screen; Marking the region as defective for commercial purposes; Marking the entire sample as defective for commercial purposes; Using the photons as the data for energy states as Read-Only memory; Change of electricity path for STM by 3D modelling evaluation; Change of electricity path for STM by 2-step electricity in a direction, then STM examination with direction.

Further, this creates a method for industrial and pharmaceutical applications: Identification, especially in inner layers, of particle materials, elements and compounds, and the boundaries of changes in such materials; Especially, identification in inner layers including a protein where the outer layer is not the critical factor. Finally, this creates a method for information system applications: The energy state of the electron becomes each electron rotation, and so the heat of electron movement is removed from the prior art electromagnetic computer systems; The examination, read-only memory, can occur by the methods of remote nodes calculated herein.

The first part of the present invention is the matching of a multiplicity of photons as the related information about an atomic structure. That it is position, orientation, and rotation information derived by analytical matching of multiple photons (or statistical interpretation of photons to get isolate the likely photon direction) from system manipulating examination to get target photon from the same molecules or atom as an information set.

This is particularly interesting in finding orientations of layers. Understanding of hidden layers is difficult with the direct reflection or frequency-abundance prior art methods.

A further part of the present invention is the atomic and molecular model based upon a further optical or electrical pulse or pulses adjusted based upon the multiplicity model to understand iteratively. The use of a computerized model to adjust further action is the proper use of computerized modelling.

A further part of the present invention is the avoidance of certain distances of entanglement nodes where predicted measurement will not activate receivers because of the inside to outside harmonics of the electron-nucleus-electron set in a target direction.

Another part of the present invention is microscopy methods to use as system of receptors and prisms to determine both direction and wavelength for a given target from the same photon or set of photons analyzed as from the same origination molecular structure.

The final portion is the application systems which combine the methods in a recursive sequence to achieve investigation, defect-marking actions. One set of these would be a photon computer when the cycles are the observation of remote information, as those electron energy states observed remotely without disturbing the memory state of the electron.

The particular embodiments disclosed above are illustrative only, as the embodiments may be modified and practiced in different but equivalent manners apparent to those skilled in the art having the benefit of the teachings herein. It is therefore evident that the particular embodiments disclosed above may be altered or modified, and all such variations are considered within the scope and spirit of the application. Accordingly, the protection sought herein is as set forth in the description. Although the present embodiments are shown above, they are not limited to just these embodiments, but are amenable to various changes and modifications without departing from the spirit thereof.

What is claimed is:

1. A system, comprising:
   a closeable container suitable to accommodate a target object inside of the closeable container, wherein the target object is for examination;
   a plurality of electrical transfer points associated with the target object, the plurality of electrical transfer points being an application of energy to generate one or more photons;
   the system configured to receive and measure electromagnetic waves from the one or more photons, and to generate a data set of information, the information including at least one of direction, wavelength, and polarity;
   the system further configured to receive the data set of information;
   generate a model of subatomic particle placement for the one or more photons by one or more sets of electron-nucleus-electrons at 180 degrees versus nucleus vertex by at least one of direction, wavelength, and polarity, as determined by the data set of information; and
   re-examine the model at one or more of a different initiation-to-destination energy path, a different measuring position, or a different energy input;
   wherein the receiving of the data set of information, generating of the model, and the re-examination of the model provides information for industrial application.

2. The system of claim 1, wherein:
   the photon direction is a line defining a geometric engineering of the one or more sets of electron-nucleus electrons;
   a photon wavelength determines a 3D internal dimension of one of the one or more sets of electron-nucleus electrons; and
   a photon polarity is a 3D rotational direction relative to the one or more sets of electron-nucleus electrons, including subshell-s.

3. The system of claim 1, further configured to:
   compare each of the plurality of electrical transfer points to a crystal or lattice structure model, the comparing being based on knowable inclination angles of subatomic particle electron-nucleus-electron sets of the crystal or lattice structure; and
   marking, based on the comparing, any of the plurality of electrical transfer points as defective or rejected.

4. The system of claim 1, further configured to:
plasticize, by utilizing a series of examination pulses and examining variability of photon direction of the series of examination pulses, each of the plurality of electrical transfer points;
comparing the plasticizing to a crystal or lattice structure model, the comparing being based on knowable inclination angles of subatomic particle electron-nucleus-electron sets of the crystal or lattice structure; and
marking, based on the comparing, any of the plurality of electrical transfer points as defective or rejected.

5. The system of claim 1, further configured to:
modify one or more inner layer data-sets of one or more inner layer target points of the plurality of electrical transfer points based upon deflection angles statistically different from one or more outer layer data sets of one or more outer layer target points of the plurality of electrical transfer points.

6. The system of claim 1, further configured to:
compare a data-set of information, including direction as it relates to inclination angles of bonds, to electron-nucleus-electron sets for atoms of proteins in sequence and 3D engineering; and
identify, based on the comparing, a specific sequence of protein segments associated with one or more inner layer target points of the plurality of electrical transfer points.

7. The system of claim 1, further configured to:
identify a single electron region of the target object as occurrence or non-occurrence for computer operations based on the model, the identification being based on electron energy level changes as a read-only memory method.

8. The system of claim 1, wherein the application of energy occurs by multiplicity of connectors, which during re-examination are switched to provide paths to a 1-atom tip via one of the plurality of electrical transfer points that pass through to inner layers of the target.

9. The system of claim 1, wherein the application of energy occurs by multiplicity of connectors, which during re-examination are switched to provide at least two paths to a 1 atom tip via the plurality of electrical transfer points that are associated with a molecule, but via different positions of both the 1 atom tip and the plurality of electrical transfer points.

10. The system of claim 1, further configured to:
calculate an energy level and a separation distance of a newly initiated electromagnetic wave associated with a photon; and
predict the photon based on the photon direction and a photon wavelength based on the data set of information and the model.

11. A system, comprising:
a lattice computer chip generated from lattice, including a base material, with differential memory behavior by doping with a atoms or molecule other than such base material;
a ribbon of conducting material placed such that electricity flows to the lattice computer chip and at a range of two to four silicon molecules away;
a microscopy for creating electrical energy flow at a plurality of positions of different 3D orientation towards the lattice computer chip, such that one or more photons are generated;
the system configured to receive and measure electromagnetic waves from the one or more photons, to generate a data set of information, the information including at least one of direction, wavelength, and polarity;
the system further configured to receive the data set of information;
generate a model of subatomic particle placement for the one or more photons by one or more sets of electron-nucleus-electrons at 180 degrees versus nucleus vertex by at last one of direction, wavelength, and polarity, as determined by the data set of information; and
re-examine the model at one or more of a different initiation position, a different measuring position, or a different energy input;
wherein the receiving of the data set of information, generating of the model, and the re-examination of the model provides information for the lattice computer chip; and wherein a direct electrical connection to the lattice computer chip occurs by multiplicity of connectors which are switched to provide at least two paths to a 1-atom tip via the lattice computer chip that occur through the same molecule, but via different positions of both the 1-atom tip and the direct electrical connection; and
wherein an intermediate electrical pulse occurs between two direct connectors in an orientation different to a direction of the 1-atom tip to direct electrical connection.

12. The system of claim 11, further configured to:
inspect, provided an inclination angle and the data set of information, for a photon in a different direction at an angle greater than 20 degrees; and
predict one or more additional target areas for examination of the lattice computer chip for different electron-nucleus-electron sets in 3D space;
wherein the data set of information includes a relative angle of a predicted electron-nucleus electron 3D orientation.

* * * * *